United States Patent [19]

Gutierrez et al.

[11] 4,058,554

[45] Nov. 15, 1977

[54] NOVEL ESTER DERIVATIVES OF ETHER POLYCARBOXYLIC ACIDS AND PROCESS FOR MAKING SAME

[75] Inventors: Eddie N. Gutierrez, Fort Lee; Vincent Lamberti, Upper Saddle River, both of N.J.

[73] Assignee: Lever Brothers Company, New York, N.Y.

[21] Appl. No.: 642,838

[22] Filed: Dec. 22, 1975

[51] Int. Cl.$^2$ ............................................. C07C 69/66
[52] U.S. Cl. ...................................... 560/180; 560/44; 560/179; 560/190; 560/60; 560/38; 560/15; 560/171; 560/154; 260/518 R; 260/519; 260/534 E; 260/535 P; 260/537 S
[58] Field of Search ...................................... 260/484 P

[56] References Cited

U.S. PATENT DOCUMENTS 3,943,165   3/1976   Lamberti .......................... 260/484 P Primary Examiner—Paul J. Killos
Attorney, Agent, or Firm—Farrell, James J.; Kenneth F. Dusyn; Melvin H. Kurtz

[57] ABSTRACT

Novel polyfunctional compounds which may be hydrolyzed to the corresponding salts, which in turn are metal sequestering agents, are disclosed, as well as a novel method for their preparation. The compounds are the reaction product obtained from the reaction of selected salts of monoalkyl esters of maleic acid with selected active hydrogen containing compounds. These products are prepared by a reaction of the starting materials in preferably a substantially anhydrous medium at an elevated temperature.

3 Claims, No Drawings

NOVEL ESTER DERIVATIVES OF ETHER POLYCARBOXYLIC ACIDS AND PROCESS FOR MAKING SAME

This invention broadly relates to novel polyfunctional compounds and a process for their preparation. The compounds may be hydrolyzed to form the corresponding salts. These salts in turn are metal sequestering agents and/or detergent builders and in the preferred embodiment are salts of substituted as well as unsubstituted carboxymethyloxysuccinic acid (CMOS). Additional compounds and processes are disclosed as alternative embodiments such as, for example, the sulfur and imino analogs of CMOS as well as selected phenoxy and hydroxyalkoxy derivatives of succinic acid.

Salts of carboxymethyloxysuccinic acid as well as other ether polycarboxylic acid salts, e.g. tri-alkali metal salts, are known detergent builders and have been considered in U.S. Pat. No. 3,692,685 and Belgian Pat. No. 782,696 granted Oct. 26, 1972 as well as applications Ser. No. 139,225 filed on Apr. 30, 1971 now abandoned and Ser. No. 274,954 filed on July 25, 1972 which is a continuation-in-part of Ser. No. 139,225 all of which are assigned to the assignee hereof and which are hereby incorporated by reference herein. Generally, these compounds have been prepared by the reaction of the mixed calcium salt of glycolic acid and maleic acid in aqueous alkaline medium with a subsequent exchange of the calcium cations with the desired metal cation. The reaction is believed to proceed according to a novel form of the Michael reaction involving a mixed polyvalent metal salt of glycolic and maleic acid as the reacting species. This reaction takes place in aqueous solution in a critical alkaline pH range and, in addition, requires the presence of polyvalent metal cations in the reaction mixture and thus cannot be carried out with alkali metal salts to the exclusion of these polyvalent metal cations.

The Michael reaction referred to above is considered thoroughly in Chapter 3 of Volume 10 of a publication entitled "Organic Reactions" edited by Roger Adams et al and published in 1959 by John Wiley & Sons Inc. In its original sense, as described in the publication, this reaction involves the addition of a donor moiety containing an alpha-hydrogen atoms in a system

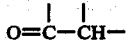

to a carbon-carbon double bond which forms part of a conjugated acceptor system of general formula

The addition proceeds under the influence of alkaline or basic catalysis.

Inherently in this reaction, the donor moiety, under the influence of the basic catalysis (sodium metal is a catalyst of choice) forms an anion which in turn reacts with the beta carbon of the acceptor system. Through the use of this reaction a series of compounds have been prepared. A listing of a large number of these reactions and reaction products appears on pages 271–544 of the above-mentioned publication. The reaction in certain selected instances does not require an added catalyst because one of the reactants contains its own basic function. The Michael reaction, thus, is an extremely useful organic tool for synthesis of selected compounds. However, disadvantages arise in attempting to prepare certain mixed esters by this route because of transesterification which can take place under the conditions of the Michael reaction thereby producing mixtures of mixed esters in correspondingly diminished yield rather than a single mixed ester in relatively high yield. Such mixtures, are normally extremely difficult to separate. These difficulties, thus, militate strongly against the use of the Michael reaction and indeed the applicability of this reaction for desired mixed ester products. Further, when the donor moiety described above is an alpha hydroxy ester, the preparation of addition compounds via the Michael reaction becomes impractical because of the dominance of the reverse Michael reaction which leads back to either the starting materials or rearranged starting materials. This is particularly true when attempting to add alpha hydroxy ester compounds across the double bond of maleic esters in the presence of alkaline catalyst.

Accordingly, an object of the present invention is to provide a process for producing novel mixed ester compounds by adding alpha hydroxy ester compounds across the double bond of selected salts of maleic acid esters, wherein the reverse Michael reaction is substantially inhibited and wherein the reaction takes place in the absence of added alkaline catalyst.

A further object is to produce compounds which by hydrolysis may be converted to substituted as well as unsubstituted carboxymethyloxysuccinic acid and salts thereof.

Yet another object of the invention is to provide a process for preparing nitrogen and sulfur analogs of substituted and unsubstituted carboxymethyloxysuccinic acid, acid esters and salts thereof.

Other objects and advantages will appear as the description proceeds.

The attainment of the above objects is made possible by this invention which includes novel compounds as well as a process for their preparation. These novel compounds have the general formula (I) as follows:

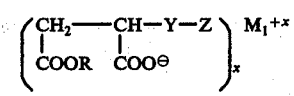

in which Y represents oxygen but in alternative embodiments may also represent sulfur or imino (NH). In formula (I), Z preferably represents the following ester moiety:

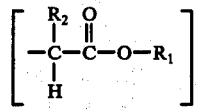

in which $R_1$ represents isopropyl or secondary butyl, i.e. a propyl or butyl group linked to the oxygen atom by a secondary carbon atom of the group, such secondary substitution is essential to facilitate the formation of the compound of formula (I) without allowing undue transesterification; and in which $R_2$ represents hydrogen as well as a methyl, ethyl or phenyl group when Y is oxygen or sulfur; and when Y is imino (NH), $R_2$ represents hydrogen, methyl, ethyl, isopropyl, isobutyl, secondary butyl, benzyl, p-hydroxybenzyl or 2-(methylthio)ethyl. Alternative embodiments of Z in formula (I) are the 2-hydroxyethyl or 3-hydroxypropyl groups. R, in formula (I), represents a primary alkyl group of one to six carbon atoms such as methyl, ethyl, propyl, butyl, pentyl or hexyl. $M_1$ in formula (I) represents hydrogen, calcium, magnesium, strontium, barium, sodium, potassium or lithium and x is equivalent to the valency of $M_1$.

Additionally, the above objects are attained by the novel process of this invention to prepare the polyfunctional compounds of formula (I). This process is preferably substantially anhydrous and includes reacting by heating a salt of a monoalkyl ester of maleic acid with an active hydrogen containing compound. The monoalkyl ester salt of maleic acid is of the general formula (II):

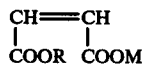

in which R is as previously defined and M represents calcium, magnesium, strontium, barium, sodium, potassium or lithium. In this process in the compound of formula (II) M cannot represent hydrogen whereas in formula (I) $M_1$ can represent hydrogen as well as the cations represented by M and thus the two separate designations of M and $M_1$ are utilized. The active hydrogen containing compound is of the general formula (III)

$$H - Y - Z \qquad (III)$$

in which Y and Z are as previously defined.

The subject invention, encompassing novel compounds and a novel process for their preparation, overcomes one or more of the disadvantages of the prior art heretofore described. This is accomplished with the advantage that such compounds may be easily prepared in good yields suitable for subsequent conversion into metal sequestering agents, preferably into salts of carboxymethyloxysuccinic acid.

The invention is hereinafter set forth in more details, specific features thereof being particularly delineated in the appended claims.

In the practice of the present invention a compound of formula (II) above is reacted preferably under substantially anhydrous conditions with a compound of formula (III) at an elevated temperature to form a reaction product which is the polyfunctional compound of formula (I).

The desired reaction product is soluble in the reaction mixture. It can be readily recovered from the reaction mixture by conventional methods such as for example insolubilizing liquid, for example, ethyl ether. Upon the addition of a sufficient amount of such an insolubilizing liquid, the product crystallizes out of solution and is readily separated from the reaction media by conventional means. Upon filtration or vacuum distillation, washing, recrystallization if desired and drying, the desired product may be obtained in purer form. The recovered product is sufficiently pure for conversion to the corresponding metal sequestrant salt.

The present invention permits the synthesis of the desired polyfunctional compound of formula (I), further, in certain cases such compounds are produced in good yield. An additional advantage of this invention is that the novel products are obtained in readily recoverable form and that the novel synthesis or process permits the formation of the product without the use of added catalyst.

The reaction of the salt of a monoalkyl ester of maleic acid of formula (II) with the active hydrogen containing compound of formula (III) proceeds preferably under substantially anhydrous conditions. The ester portion of the maleic acid salt will hydrolyze, depending on the amount of water present and for this reason water deleteriously affects the yield and is therefore best kept at a minimum. This can be done by drying the reactants and the medium before hand by conventional means.

Generally, the reaction of the above described compounds of formulae (II) and (III) to produce the novel compounds of formula (I) proceeds at elevated temperatures in the range of about 25° C to 200° C and more preferably about 100° C to 160° C. The actual reaction temperature will depend on whether a solvent is employed and the mutual solubilities of the reactants. Thus, if dimethyl formamide is utilized as the solvent or co-solvent, a temperature as low as room temperature (about 25° C) to about 100° C can be utilized whereas if the active hydrogen containing compound of formula (II) is utilized in excess as both solvent and reactant higher temperatures up to about 200° C may be employed. Generally while reflux temperatures are normally operable, it is desirable to keep the temperature in the range of about 100° C to 160° C to maintain reasonable reaction rates and to avoid the reverse Michael reaction and other decomposition reactions which tend to take place at higher temperatures.

The time necessary to complete the reaction is not critical. It will depend on temperature, on the nature of the reactants, the solvent used, if any, concentration of the reactants and the homogeneity of the system. Generally about one to three hours is sufficient to obtain maximum yield. In some cases such as the reaction involving isopropyl glycolate, a substantial yield results in about one half hour.

The reaction takes place preferably in the liquid phase. Generally, the active hydrogen containing compound of formula (III) is a liquid and will dissolve the monoester compound of formula (II). Since an excess of the reactant of formula (III) is beneficial to the reaction it is a preferred mode as side reactions and minimized and eventual separation of the components is easier. Suitable esters of formula (III), e.g. isopropyl glycolate, isopropyl lactate, isopropyl mandelate, secondary butyl glycolate, secondary butyl mandelate, isopropyl alpha hydroxy butyrate and the like may be utilized. Additionally, a cosolvent for both reactants may be used instead of an excess of the formula (III) compound provided the co-solvent does not contain an active hydrogen which will compete with the formula (III) compound and provided the co-solvent dissolves the reactants sufficiently to facilitate the reaction. Suitable solvents are, for example, dimethylformamide, dimethylacetamide and dimethyl sulfoxide.

The reaction product obtained by the above procedue is the compound of formula (I), which as previously stated can be separated from the reaction mixture by conventional means.

The compound of formula (I) may be hydrolyzed under either acidic or basic conditions to obtain either the free acid form or the salt form as represented by formula (IV) as follows:

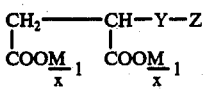

wherein Y represents oxygen but in alternative embodiments may also represent sulfur or imino (NH); Z preferably represents 1. the following moiety

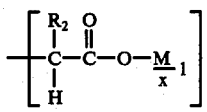

which may be either a carboxylic moiety when $M_1$ is H or a carboxylate moiety when $M_1$ represents sodium, potassium, lithium, calcium, magnesium, barium or strontium wherein $R_2$ is hydrogen, methyl, ethyl or phenyl and $x$ is 1 when $M_1$ is hydrogen or alkali metal and 2 when $M_1$ is alkaline earth metal, or 2. 2-hydroxyethyl or 3-hydroxypropyl.

Desirably alkaline hydrolysis may be carried out by different methods depending on the cation desired in the final hydrolyzed product. When the cation $M_1$ associated with the compound of formula (I) is alkaline earth it is first desirable to replace this cation with hydrogen by conventional treatment with an ion exchange resin or with an alkali metal by treatment with an aqueous solution of an alkali metal carbonate which exchanges the cation and precipitates the alkaline earth metal as the carbonate which can then be removed by filtration. If sufficient alkali metal carbonate is used, then upon heating the aqueous mixture all of the ester groups are hydrolyzed while at the same time the alkaline earth metal carbonate is precipitated. Alternatively, the compound of formula (I) wherein $M_1$ is H, obtained by treatment with ion exchange resin as described above, may be further treated with an alkali metal hydroxide to neutralize the free carboxyl group and to hydrolyze the remaining ester groups.

In another embodiment when $M_1$ is alkaline earth metal cation in the compound of formula (I) the ester groups may be hydrolyzed directly with an alkaline earth metal hydroxide to produce the corresponding alkaline earth metal salts of formula (IV) which in turn may be conventionally treated with ion exchange resins to achieve the free acid form of formula (IV). In the special case where $M_1$ of formula (I) is Ba, Ca or Sr the compound may be acidified with a stoichiometric amount of sulfuric acid to precipitate the alkaline earth metal sulfate which may then be filtered off to leave behind the compound of formula (I) where $M_1$ is H. This formula (I) compound may then be treated as described above to produce the acid and salt forms of formula (IV).

Alkaline hydrolysis is accomplished by heating the compounds of formula (I) with an alkali or alkaline earth metal, hydroxide or alkali metal carbonate. The basic hydrolysis is carried out at a temperature of about 25° C to about 100° C, preferably 40° C to 60° C.

The pH of this hydrolysis is 9 to 12 and preferably 10 to 11.

The compounds of formula (IV) wherein $M_1$ is H may be obtained in solutions having a concentration of about 1 to 50% by weight, preferably about 10 to 30% by weight, directly by acid hydrolysis of the compounds of formula (I). This hydrolysis is accomplished by using about a 0.5 to 2% by weight solution of a mineral acid such as, for example, hydrochloric, sulfuric, phosphoric and the like, preferably sulfuric to facilitate separation. The temperature utilized are generally about 25° C to 100° C preferably 50° C to 100° C. The amount of acid required must be enough to neutralize the alkali metal or alkaline earth metal of formula (I) and to provide an excess to catalyze the hydrolysis. This excess calculated on an anhydrous basis is generally about 10% by weight of the compound of formula (I) used. Isolation of the formula (IV) compound wherein $M_1$ is H is carried out after neutralization of the excess mineral acid utilized by conventional techniques such as solvent precipitation, evaporation of the solution to dryness followed by extraction by a suitable solvent such as acetone, ethyl ether and the like. The preferred temperature and pH ranges are used to obtain reasonable reaction rates and to avoid reverse Michael reactions. Isolation of the salts of formula (IV) obtained as described above is carried out by conventional techniques such as solvent precipitation, drying and recrystallization from suitable solvents such as alcohol-water.

The salts of the monoalkyl ester of maleic acid employed in the process of this invention are prepared by treating a monoalkyl ester of maleic acid with a base. The monoalkyl ester of maleic acid is in turn readily available by reacting maleic anhydride with a lower alkyl alcohol having 1 to 6 carbon atoms, for example, methanol, ethanol, propanol, butanol, pentanol or hexanol. More specifically, maleic anhydride may be dissolved in the alcohol either at room temperature or by heating at an elevated temperature, e.g. 50° C to 60° C. Addition of the appropriate base, i.e. alkali metal or alkaline earth metal hydroxide such as sodium or potassium hydroxide or magnesium barium, strontium or calcium hydroxide to a pH of about 7 to 9, neutralizes the acid portion of the molecule to produce the desired salt of formula (II). The monoalkyl maleate salt thus prepared is separated from the reaction mixture by conventional techniques, e.g. distilling off the alcohol under reduced pressure, or crystallization from the appropriate alcohol.

The active hydrogen containing compounds of formula (III) are known compounds. Glycolate esters are particularly preferred wherein the substituents of formula (III) are as follows:

Y is oxygen, $R_1$ is isopropyl or secondary butyl and $R_2$ is hydrogen, methyl, ethyl or phenyl.

In addition, according to another embodiment of the invention, analogs of carboxymethyloxysuccinic acid can also be prepared with the instant process by utilizing other active hydrogen containing compounds such as alpha-hydroxy carboxylic esters, alpha-amino carboxylic esters and alpha-thiol carboxylic esters in place of the glycolate esters described above.

Examples of other alpha-hydroxy carboxylic esters which can be employed in the practice of this invention are esters derived from lactic acid, alpha-hydroxy butyric acid and mandelic acid.

The nitrogen analogs of the compound of formula (I) that can be prepared by the process of this invention are prepared from esters of alpha-amino carboxylic acids, for example, esters derived from glycine, alanine, valine, leucine, isoleucine, phenylalanine, tyrosine, methionine and the like. It will be readily understood that when the esters of alpha amino acids (i.e., for example, the above series glycine through methionine inclusive) are used, $R_2$ in formula (I) will represent, respectively, hydrogen, methyl, isopropyl, isobutyl, secondary butyl, benzyl, p hydroxybenzyl or 2-(methylthio)ethyl groups.

The sulfur analogs can be prepared by substituting alpha-thiol carboxylic esters, for example, esters of thioglycolic acid also referred to as mercapto acetic acid, in place of the glycolate esters described above.

Representative compounds of formula (I) prepared according to the process of the invention include 1. Sodium [(1-carboisopropoxy-3-carboxylate-4-carbomethoxy)-2-oxabutane]

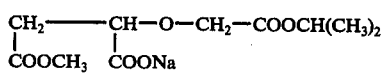

2. Potassium [(1-carboisopropoxy-3-carboxylate-4-carbomethoxy)-2-oxabutane]

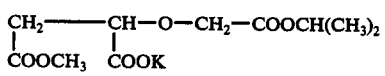

3. Calcium bis[(1-carboisopropoxy-3-carboxylate-4-carbomethoxy)-2-oxabutane]

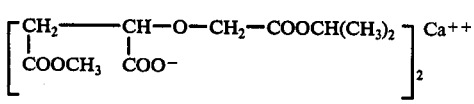

4. Magnesium bis[(1-carboisopropoxy-3-carboxylate-4-carbomethoxy)-2-oxabutane]

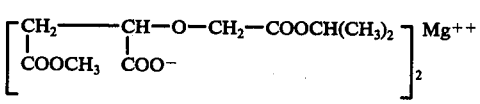

5. Sodium [(2-carboisopropoxy-4-carboxylate-5-carbomethoxy)-3-oxapentane]

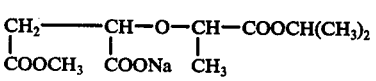

6. Potassium [(2-carboisopropoxy-4-carboxylate-5-carbomethoxy)-3-oxapentane]

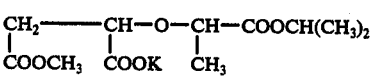

7. Calcium bis[(2-carboisopropoxy-4-carboxylate-5-carbomethoxy)-3-oxapentane]

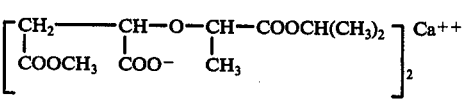

8. Magnesium bis[(2-carboisopropoxy-4-carboxylate-5-carbomethoxy)-3-oxapentane]

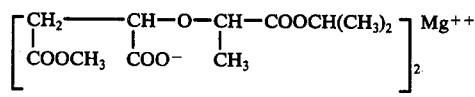

9. Sodium [(3-carboisopropoxy-5-carboxylate-6-carbomethoxy)-4-oxahexane]

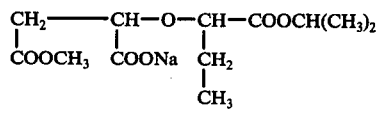

10. Potassium [(3-carboisopropoxy-5-carboxylate-6-carbomethoxy)-4-oxahexane]

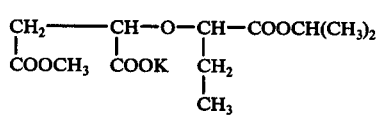

11. Calcium bis[(3-carboisopropoxy-5-carboxylate-6-carbomethoxy)-4-oxahexane]

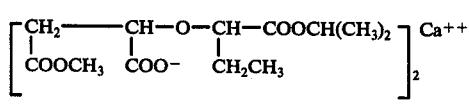

12. Magnesium bis[(3-carboisopropoxy-5-carboxylate-6-carbomethoxy)-4-oxahexane]

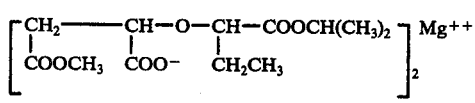

13. Sodium [(1-phenyl-1-carboisopropoxy-3-carboxylate-4-carbomethoxy)-2-oxabutane]

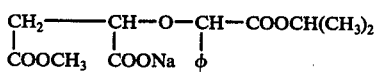

14. Calcium bis[(1-phenyl-1-carboisopropoxy-3-carboxylate-4-carbomethoxy-2-oxabutane]

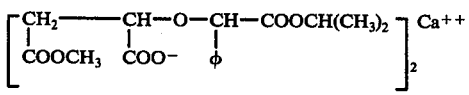

15. Sodium [(1-carboisopropoxy-3-carboxylate-4-carbomethoxy)-2-azabutane]

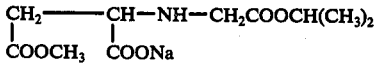

16. Sodium [(2-carboisopropoxy-4-carboxylate-5-carbomethoxy)-3-azapentane]

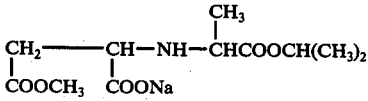

17. Calcium bis[(1-carboisopropoxy-3-carboxylate-4-carbomethoxy)-2-azabutane]

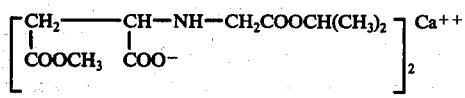

18. Calcium bis[(1-carboisopropoxy-3-carboxylate-4-carbomethoxy)-2-thiabutane]

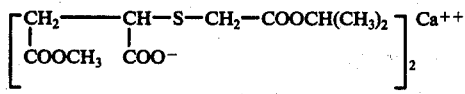

19. Calcium bis[methyl (1-phenaza)succinate]

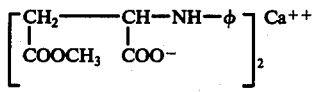

20. Calcium bis[(1-hydroxy-4-carboxylate-5-carbomethoxy)-3-oxapentane]

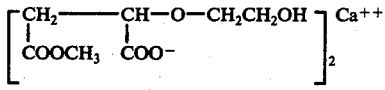

21. Calcium bis[(1-carboisopropoxy-3-carboxylate-4-carbomethoxy)-2-oxabutane]

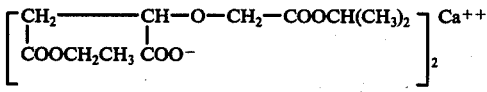

The following examples will more fully illustrate the embodiments of this invention. All parts and proportions referred to herein and in the appended claims are by weight unless otherwise indicated.

EXAMPLE I

A. PREPARATION OF ISOPROPYL GLYCOLATE 100 grams of glycolic acid is dissolved in 250 ml of isopropanol containing 15 ml of concentrated sulfuric acid. The solution is refluxed for 10 hours, neutralized with calcium carbonate to pH 6 and then filtered to remove the precipitated calcium sulfate. The filtrate is then evaporated on the hot water bath at reduced pressure to remove excess isopropanol and the residue distilled in vacuo to give the product, isopropyl glycolate, b.p. 75°–80° C (30 mm).

Sec-butyl glycolate is prepared in the same manner as above but using sec-butanol in place of the isopropanol.

B. PREPARATION OF CALCIUM BIS(METHYL MALEATE)

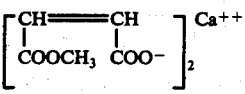

One mole of maleic anhydride is dissolved with stirring in 1000 ml methanol at 50°–60° C. The mixture is cooled to 25° C and with the aid of a pH meter, the pH is adjusted to 8.6 with calcium hydroxide while maintaining the temperature below 25° C with an ice bath. 149 g of calcium bis(methyl maleate) is recovered by crystallizing out of methanol followed by drying in a vacuum oven.

C. PREPARATION OF CALCIUM BIS[(1-CARBOISOPROPOXY-3-CARBOXYLATE-4-CARBOMETHOXY)-2-OXABUTANE]

200 grams (1.7 moles) of isopropyl glycolate and 50 grams (0.33 moles) of calcium bis(methyl maleate) are first heated to 100° C to dissolve the salt. The reaction mixture is then heated to reflux (150° C) for 2 hours. After cooling the reaction to room temperature, ether is added to the solution to precipitate a solid material which is filtered and washed with ether; 47 g of solid (Product A) is obtained. The ether layer also contains additional product in the form of the acid. The ether solution is evaporated on a roto evaporator and the resulting viscous liquid is dissolved in water and neutralized to a pH of 7.0 with calcium hydroxide to form the salt. The water is removed on the roto evaporator, the residue taken up in ether and the precipitated solid filtered; 19 g of product (Product B) is obtained. NMR analysis of Products A and B using potassium acid phthalate as an internal standard confirmed that Product A contained 92.5% of the desired product and Product B contained 80.7% of the desired product. The total yield of the desired product, i.e. calcium bis[(1-carboisopropoxy-3-carboxylate-4-carbomethoxy)-2-oxabutane] is 66 g total of Products A and B, which is 66.7% actual yield.

D. PREPARATION OF THE TRISODIUM SALT OF CARBOXYMETHYLOXYSUCCINIC ACID BY SAPONIFICATION OF CALCIUM BIS[(1-CARBOISOPROPOXY-3-CARBOXYLATE-4-CARBOMETHOXY)-OXABUTANE-2]

Three grams (0.011 mole) of calcium bis[(1-carboisopropoxy-3-carboxylate-4-carbomethoxy)-2-oxabutane] (Product A from step B above) is saponified using 0.048 mole sodium hydroxide. After heating to 50° C for 2-3 hours, the solution is neutralized to pH 7 with $H_2SO_4$ to precipitate calcium as $CaSO_4$. Sodium carbonate (0.5 g) is then added to raise the pH to 8.6 and to precipitate out any remaining calcium as calcium carbonate. The solution is filtered and the filtrate is evaporated to dryness. The trisodium salt of carboxymethyloxysuccinic acid is obtained in a yield of 2.7 g; the NMR of this product is identical to that of the trisodium salt obtained by the preparative method disclosed in U.S. Pat. No. 3,692,685.

E. PREPARATION OF CALCIUM BIS[(2-CARBOISOPROPOXY-3-CARBOXYLATE-4-CARBOMETHOXY)-2-OXABUTANE]

The product of B above is prepared in the same manner except that certain parameters are changed. The mole ratio of maleate to glycolate is 0.17:1, calcium hydroxide solution is added to the reaction mixture to a pH of 8.6 and the reaction is run for 2-3 hours. The solid product which precipitates out on addition of ether contains 87.7% of calcium bis[(1-carboisopropoxy-3-carboxylate-4-carbomethoxy)-2-oxabutane] and the viscous liquid product contains 71.8% of the monoacid product. The total yield of product calculated as the calcium salt is 69.2% of the theoretical.

EXAMPLE II

A. PREPARATION OF MAGNESIUM BIS(METHYL MALEATE)

Fifty grams of maleic anhydride is dissolved in 200 ml methanol and magnesium hydroxide is added to a pH of 7.3. The solution is filtered, the methanol is distilled off and the product is dried under vacuum. An NMR analysis of the product taken using potassium acid phthalate as the standard indicates that the product contains 78.7% magnesium bis(methyl maleate).

B. MAGNESIUM BIS[(1-CARBOISOPROPOXY-3-CARBOXYLATE-4-CARBOMETHOXY)-2-OXABUTANE]

Five grams (0.03 moles) of dried magnesium bis(methyl maleate), the dried product from A above having an 85.3% purity is placed into 11 grams of isopropyl glycolate and the solution is heated to 85°-90° C for 2 hours and then to 100°-105° C for one hour. The excess glycolate is removed under vacuum and the residue is extracted twice with ether leaving the ether insoluble solid product. Seven grams of this solid, magnesium bis[(1-carboisopropoxy-3-carboxylate-4-carbomethoxy)-2-oxabutane], is obtained; evaporation of the combined ether extracts affords 2.1 grams of a liquid 52.5% product as the acid. This acid can in turn be converted to the desired magnesium salt product by neutralization with Mg(OH)$_2$. The total yield of product is 80% of theory based on the dry solid salt and the acid assuming 100° conversion of the acid to the salt upon neutralization.

EXAMPLE III

PREPARATION OF MAGNESIUM BIS[(2-CARBOISOPROPOXY-4-CARBOXYLATE-5-CARBOMETHOXY)-3-OXAPENTANE]

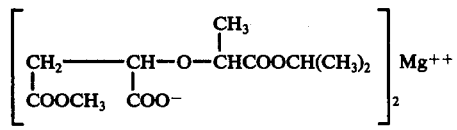

Five grams (0.028 moles) of magnesium bis(methyl maleate) prepared as in Example II(A) is placed into 32 grams (0.27 moles) isopropyl lactate. The solution is heated to 110°-115° C for two hours and the isopropyl lactate distilled off under reduced pressure. The residue is extracted twice with ether. Seven grams of ether insoluble solid magnesium bis[(2-carboisopropoxy-4-carboxylate-5-carbomethoxy)-3-oxapentane] is obtained. The NMR analysis of this material using potassium acid phthalate as an internal standard is as follows:

67.7% magnesium bis[(2-carboisopropoxy-4-carboxylate-5-carbomethoxy)-3-oxapentane]
19.6% magnesium bis(methyl maleate)
9.3% magnesium maleate
10.5% water The ether extract containing a portion of the mono-acid of the desired salt is evaporated to dryness and 4 grams of solid collected which contains 48.2% of the mono-acid. This mono-acid can be converted to the desired salt product by dissolving the solid in water and adding Mg(OH)$_2$ to a pH of 7.3. The total yield of product assuming 100% conversion of the mono-acid is 70%.

EXAMPLE IV

A. PREPARATION OF SODIUM METHYL MALEATE 1 mole of maleic anhydride is dissolved in 1000 ml methanol and 0.5 mole of sodium carbonate is added. The solution is filtered and the methanol is distilled off under pressure. After drying the product in a vacuum oven 152 g of sodium methyl maleate is obtained.

B. PREPARATION OF SODIUM [(1-CARBOISOPROPOXY-3-CARBOXYLATE-4-CARBOMETHOXY)-2-OXABUTANE]

160 grams (1.3 moles) of isopropyl glycolate and 50 grams (0.43 moles) of sodium methyl maleate referred in A above are heated to reflux for 2 hours, then the excess glycolate is distilled off under vacuum. The residue is dissolved in methanol and steam distilled to remove both the methanol and traces of isopropyl glycolate. The resulting water solution is evaporated to dryness and the viscous material obtained is taken up in isopropanol, a portion of the material dissolves and another portion precipitates. The solid precipitate is filtered and 21 grams recovered. NMR analysis of the solid shows a mixture of disodium maleate and product. The isopropanol is evaporated off from the filtrate and the viscous liquid remaining is dissolved in water and neutralized to pH 8.3 using 0.1N sodium hydroxide. The solution is then evaporated down to dryness to give a residue of 35.3 grams containing 52.1% sodium (1-carboisopropoxy-3-carboxylate-4-carbomethoxy)-2-oxabutane (by NMR). The total yield of the desired sodium salt obtained is 27.8% of theory.

EXAMPLE V

PREPARATION OF CALCIUM BIS[(1-CARBOISOPROPOXY-3-CARBOXYLATE-4-CARBOMETHOXY)-2-THIABUTANE]

A solution of 8 g (.053 moles) of calcium bis(methyl maleate) prepared as in Example I and 25 g of isopropyl mercaptoacetate (.19 moles) is refluxed for one hour. Excess mercaptoacetate is distilled off under vacuum and ether is added to the residue to precipitate the produce and extract residual mercaptoacetate ester. The product, calcium bis[(1-carboisopropoxy-3-carboxylate-4-carbomethoxy)-2-thiabutane], is obtained in 95% yield (14.3 g). The structure is confirmed by NMR analysis.

The following compounds are similarly prepared by the above procedure: magnesium bis[(1-carboisopropoxy-3-carboxylate-4-carbomethoxy)-2-thiabutane and sodium [(1-carboisopropoxy-3-carboxylate-4-carbomethoxy)-2-thiabutane] by substituting magnesium bis(methyl maleate) prepared as in Example II(A) and sodium methyl maleate prepared in Example IV(A) respectively in place of calcium bis(methyl maleate).

EXAMPLE VI

CALCIUM BIS[(1-CARBOISOPROPOXY-3-CARBOXYLATE-4-CARBOMETHOXY)-2-AZABUTANE]

Calcium bis(methyl maleate) prepared as in Example I(A), 10 grams (.067 moles) and 28 grams (.15 moles) of isopropyl glycinate are heated for one hour at 80° C. After removing the excess glycinate ester by distilling under vaccum, the reaction mixture is extracted with ether. The resulting ether insoluble solid material is filtered and immediately placed in a vacuum oven since it is hygroscopic. Nine grams of solid product, 50% yield, of calcium bis[(1-carboisopropoxy-3-carboxylate-4-carbomethoxy)-2-azabutane] is obtained. The structure of the product is confirmed by NMR.

The following compounds are similarly prepared by the above procedure: magnesium bis[(1-carboisopropoxy-3-carboxylate-4-carbomethoxy)-2-azabutane] and sodium [(1-carboisopropoxy-3-carbomethoxy)-2-azabutane] by substituting magnesium bis(methyl maleate) prepared as in Example II(A) and sodium methyl maleate prepared as in Example IV(A) respectively in place of calcium bis(methyl maleate).

EXAMPLE VII

PREPARATION OF CALCIUM BIS[METHYL 1-PHENAZASUCCINATE]

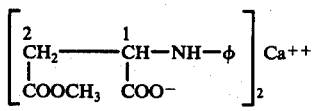

7.0 grams (0.05 moles) of calcium bis(methyl maleate) prepared as in Example I(A) and 25 grams (0.27 moles of aniline are heated to 100° C for one hour, cooled to 25° C and either is added to precipitate out solid. 9.5 grams of calcium bis[methyl 1-phenazasuccinate] is obtained in 38% yield.

EXAMPLE VIII

PREPARATION OF CALCIUM BIS[(1-CARBOISOPROPOXY-3-CARBOXYLATE-4-CARBOMETHOXY)-2-OXABUTANE]

4 grams (0.027 mole) of calcium bis(methyl maleate) prepared as in Example I(A) is added to 13 grams (0.11 moles) of isopropyl glycolate, 100 grams of dimethylformamide (DMF) solvent and 1 gram of Ca(OH)$_2$. The mole ratio of maleate to glycolate is 0.25 to 1. The solution is stirred at room temperature for 3 hours, residual Ca(OH)$_2$ is filtered out and the DMF and excess glycolate are distilled off under reduced pressure. The residue is dissolved in acetone and ether is added to precipitate the desired salt. This product is filtered and dried in a vacuum oven; 3 grams (26% yield) are recovered. Analysis of the product by NMR using a potassium acid phthalate internal standard is as follows:

62.7% calcium bis[(1-carboisopropoxy-3-carboxylate-4-carbomethoxy)-2-oxabutane]
22.7% calcium maleate A confirmation analysis was run utilizing G.L.C. (gas liquid chromatography). The salt, i.e. the calcium bis[(1-carboisopropoxy-3-carboxylate-4-carbomethoxy)-2-oxabutane] is dissolved in methanol, acidified with concentrated H$_2$SO$_4$ and refluxed for 3 hours. The solution is neutralized, filtered and the methanol removed by distillation under reduced pressure. The G.L.C. analysis shows:

54.7% of the trimethyl ester of carboxymethyloxysuccinic acid*
25.8% dimethyl maleate
5.3% dimethyl fumarate

*The retention time of this material is identical to that of the authentic triester prepared according to method disclosed in Belgium Pat. No. 802,356 (application number 1334496) granted Jan. 14, 1974.

EXAMPLE IX

PREPARATION OF CALCIUM BIS[(1-PHENYL-1-CARBOISOPROPOXY-3-CARBOXYLATE-4-CARBOMETHOXY)-2-OXABUTANE]

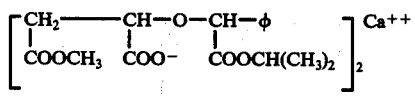

12 grams (.08 moles) of calcium bis(methyl maleate) prepared as in Example I(A) and 60 grams (0.3 moles) of isopropyl mandelate are mixed and heated to 130° C for 2 hours. The solution is cooled to room temperature. The ether is added (at 25° C) and the ether insoluble solid precipitates and is filtered off. 12.5 grams of product is obtained. Since the solid is water insoluble 8 grams hydrochloric acid is added to the suspended solid in H$_2$O to convert the product to the acid form in order to separate it from other impurities and in order to dissolve it in CDCl$_3$ for NMR analysis. A water immiscible liquid separates out and is extracted out with ether. 4 grams of the mono-acid precursor of calcium bis[(1-phenyl-1-carboisopropoxy-3-carboxylate-4-carbomethoxy)-2-oxabutane], i.e. 12.5% yield is obtained.

EXAMPLE X

PREPARATION OF CALCIUM BIS[(3-CARBOISOPROPOXY-5-CARBOXYLATE-6-CARBOMETHOXY)-4-OXAHEXANE]

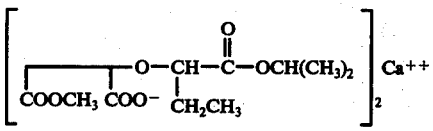

6 grams (0.04 moles) of calcium bis(methyl maleate) prepared as in Example I(A) and 26.5 g of alpha-hydroxy isopropyl butyrate are heated to 130° C for 2 hours. The excess butyrate solvent is then removed under reduced pressure and is extracted with ether. The ether insoluble salt precipitates and is filtered out. Five grams of solid is collected.

The compound was converted to the sodium salt by addition of sodium carbonate in order to make it more soluble in D$_2$O for NMR analysis. The analysis is as follows:

41.0% [(3-carboisopropoxy-5-carboxylate-6-carbomethoxy)-4-oxahexane] which corresponds to % calculated as the desired calcium salt
16.4% calcium bis(methyl maleate)
21.1% calcium maleate
11.4% water

EXAMPLE XI

PREPARATION OF CALCIUM BIS[(1-HYDROXY-4-CARBOXYLATE-5-CARBOMETHOXY)-3-OXAPENTANE]

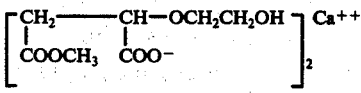

Seven grams (.047 moles) of calcium bis methyl maleate prepared as in Example I(A) is dissolved in 25 grams (0.4 moles) of ethylene glycol and the reaction mixture heated to 105° C for 3 hours. The solution is then cooled (some product is insoluble) and the solution is extracted 5-6 times with acetone until all of the ethylene glycol is extracted out. 5.7 grams of crystalline solid is obtained (58% yield). This solid is converted to the sodium salt for NMR identification by dissolving the solid in D₂O and adding sodium carbonate to precipitate the calcium as calcium carbonate.

EXAMPLE XII

A. PREPARATION OF CALCIUM BIS(ETHYL MALEATE)

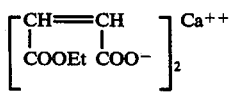

Fifty grams of maleic anhydride is dissolved in 400 mls ethyl alcohol. Ca(OH)₂ is added to a pH of 8.5, filtered and dried in a dessicator over P₂O₅.

The product is 99.1% pure by NMR analysis.

B. PREPARATION OF CALCIUM BIS[(1-CARBOISOPROPOXY-3-CARBOXYLATE-4-CARBOETHOXY)-2-OXABUTANE]

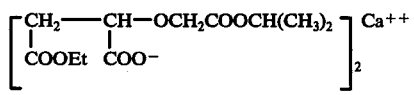

Twelve grams (.07 moles) of calcium bis(methyl maleate) prepared as in Example XIII(A) above is added to 40 grams (.34 moles) of isopropyl glycolate and the reaction mixture is heated to 140°-150° C for one hour. The glycolate solvent is distilled off under reduced pressure and the residue is extracted with ether. 6.2 grams of ether insoluble solid calcium bis[(1-carboisopropoxy-3-carboxylate-4-carboethoxy)-2-oxabutane] is obtained. The ether layer contains 13 grams of a viscous liquid containing the product in the form of the acid which can be converted to the desired salt by dissolving in water and adding Ca(OH)₂ to a pH of 8.6 then taking to dryness and extracting with ether. The salt is ether insoluble. Both the solid and the viscous liquid are analyzed by NMR, the results are as follows:

SOLID ANALYSIS 90.8% of calcium bis[(1-carboisopropoxy-3-carboxylate-4-carboethoxy)-2-oxabutane]
7.4% calcium maleate
1.8% water

VISCOUS LIQUID ANALYSIS 56.8% of calcium bis[(1-carboisopropoxy-3-carboxylate-4-carboethoxy)-2-oxabutane] (as the acid)

The total yield of the product assuming 100% conversion of the acid to the desired salt is 70%.

EXAMPLE XIII

ATTEMPTED PREPARATION OF TRIETHYL CARBOXYMETHYLOXYSUCCINATE VIA THE NORMAL MICHAEL REATION

Into 100 grams ethanol is placed 0.2 g sodium until the reaction is complete. 10.6 g ethyl glycolate is added and the ethanol distilled under reduced pressure. 15 g diethyl maleate is added the reaction mixture heated to 45° C for one hour.

The product is taken up in ether and the insoluble solid is filtered. The solution is distilled under reduced pressure to remove ether and unreacted glycolate. Recovered 16 grams of product(s).

GLC analysis (% by weight)
6.0 ethyl glycolate
87.6 diethyl fumarate
1.2 diethyl maleate
1.9 triethyl carboxymethyloxysuccinate. Corresponds to a 7.5% yield.

EXAMPLE XIV

A. PREPARATION OF BARIUM BIS(METHYL MALEATE)

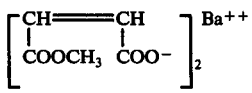

Thirty grams of maleic anhydride is dissolved in 400 moles of methanol and Ba(OH)₂ is added to a pH of 8.0. The solution is filtered and is taken down to dryness. NMR analysis is as follows:
79.1% of barium bis(methyl maleate)
20.9% water

B. PREPARATION OF BARIUM BIS[(1-CARBOISOPROPOXY-3-CARBOXYLATE-4-CARBOMETHOXY)-2-OXABUTANE]

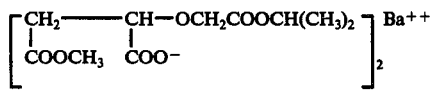

Nineteen grams (0.08 moles) of barium bis(methyl maleate) prepared as in A above is placed into 55 grams (0.47 moles) of isopropyl glycolate and the solution is heated to 140°-145° C (some solid remained undissolved).

The glycolate solvent is removed under reduced pressure and the residue is extracted with ether and filtered. 2.5 grams of ether insoluble barium bis[(1-carboisopropoxy-3-carboxylate-4-carbomethoxy)-2-oxabutane] is filtered off. The ether solution is taken to dryness and 30.3 g of a highly viscous liquid is obtained. NMR analysis using potassium acid phthalate as a standard gives the following results:

SOLID 90.8% barium bis[(1-carboisopropoxy-3-carboxylate-4-carbomethoxy)-2-oxabutane]
7.4% barium maleate
1.8% water

VISCOUS LIQUID 35.7% (1-carboisopropoxy-3-carboxylic acid-4-carbomethoxy)-2-oxabutane
54.7% barium maleate
9.6% isopropyl glycolate The acid can be converted to the desired product by raising the pH of the liquid to 8.5 with Ba(OH)₂. The total yield assuming 100% conversion of the acid to the salt is 56.7%.

EXAMPLE XV

A. PREPARATION OF CALCIUM BIS(HEXYL MALEATE)

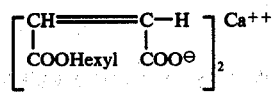

40 grams (0.4 moles) of maleic anhydride is dissolved in 200 grams hexanol and Ca(OH)$_2$ is slowly added with stirring until a pH of 8.5-8.6 is reached. The solution is filtered and taken to dryness. The residue is taken up in acetone and the first crop of solid is filtered. (This crop is contaminated with calcium maleate.) The second crop of crystals which slowly precipitates out is filtered and dried. The calcium bis(hexyl maleate) is 90% pure by NMR analysis.

B. PREPARATION OF CALCIUM BIS[(1-CARBOISOPROPOXY-3-CARBOXYLATE-4-CARBOHEXYLOXY)-2-OXABUTANE]

10 grams (.04 moles based on 90% purity of the product produced in A above is dissolved in 35 grams (0.3 moles) of isopropyl glycolate and the mixture heated to 140-150° C for 45 minutes. The excess glycolate solvent is distilled off under reduced pressure and the viscous liquid extracted twice with 200 grams of water to remove any dissolved glycolate. 15 grams of a very viscous liquid are collected containing 42.4% of calcium bis[(1-carboisopropoxy-3-carboxylate-4-carbohexyloxy)-2-oxabutane]. The yield is 49%.

EXAMPLE XVI

A. PREPARATION OF STRONTIUM BIS(METHYL)MALEATE

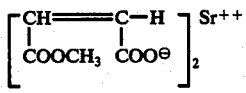

Thirty-five grams (0.35 moles) of maleic anhydride is dissolved in 300 grams methanol and Sr(OH)$_2$ is added slowly with stirring to a pH of 8.5. The solution is evaporated under reduced pressure to a tacky residue. 100 mls of methanol is added and the first crop of crystals filtered. To the methanol solution is added 200 mls acetone and 300 mls ether and the resulting solution is stirred for five minutes. The solvent is decanted and the residue triturated with 100 mls methanol, 200 mls acetone and 200 mls ether. The solid remained is filtered, washed with acetone and dried in the vacuum oven. Forty-six grams of strontium bis(methyl)maleate is obtained having a purity of 85.6% by NMR analysis using potassium acid phthalate as an internal standard.

B. PREPARATION OF STRONTIUM BIS[(1-CARBOISOPROPOSY-3-CARBOXYLATE-4-CARBOMETHOXY)-2-OXABUTANE]

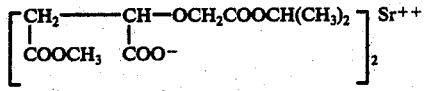

17.5 grams (0.09 moles based on 85.6% to purity) of the product of A above is placed into 51 grams (0.43 moles) of isopropyl glycolate and the solution heated to 140°-150° C for one hour. The isopropyl glycolate is distilled off under reduced pressure and the residue is extracted with one liter of ether. The solid ether insoluble product is dried in a vacuum oven to constant weight. 17.8 grams of strontium bis[(1-carboisopropoxy-3-carboxylate-4-carbomethoxy)-2-oxabutane] is obtained. The ether layer is taken down to dryness and 13.8 grams of liquid is obtained. This liquid is the mono-acid of the desired salt and can be converted to the desired salt by dissolving it in water, adding Sr(OH)$_2$ to a pH of 8.5, evaporating to dryness and extracting with ether. The solid and liquid were analyzed by NMR as follows:

SOLID 77.5% strontium bis[(1-carboisopropoxy-3-carboxylate-4-carbomethoxy)-2-oxabutane]
10.1% strontium maleate
10.5% strontium bis(methyl)maleate

LIQUID 30.0% (1-carboisopropoxy-3-carboxylic acid-4-carbomethoxy)-2-oxabutane
70.0% isopropyl glycolate The yield is 70.8% based on 100% conversion of the mono-acid present to the desired salt product.

This invention has been described with respect to certain preferred embodiments, and various modifications and variations in the light thereof will be suggested to persons skilled in the art and are to be included within the spirit and purview of this application and the scope of the appended claims.

What is claimed is:

1. A compound of the general formula

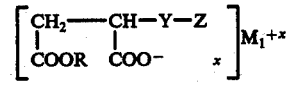

wherein R is a primary alkyl group of one to six carbon atoms,
wherein M$_1$ is H, Ca, Mg, Ba, Sr, Na, K or Li,
wherein x is 1 or 2 and is equivalent to the valency of M$_1$,
wherein Y is oxygen, and
wherein Z is
1. an ester moiety of the general formula:

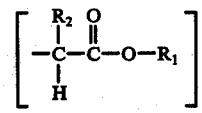

wherein R$_1$ is isopropyl or secondary butyl, and
wherein R$_2$ is hydrogen, methyl or ethyl.

2. A compound as defined in claim 1 having the formula

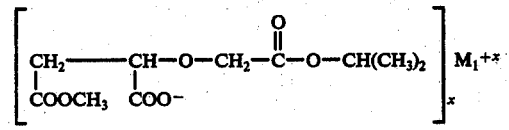

wherein said M$_1$ and x are as previously defined.

3. A compound as defined in claim 1 having the formula
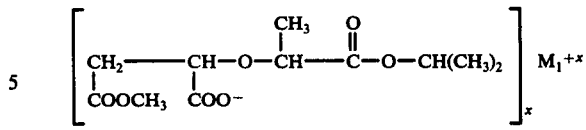
wherein said $M_1$ and $x$ are as previously defined.

UNITED STATES PATENT AND TRADEMARK OFFICE
CERTIFICATE OF CORRECTION

PATENT NO. : 4,058,554
DATED : November 15, 1977
INVENTOR(S) : Eddie N. Gutierrez, et al.

It is certified that error appears in the above-identified patent and that said Letters Patent are hereby corrected as shown below:

In the Specification:

Col. 11, line 32: "100°" should read -- 100% --.

In the Claims:

Claim 1, Col. 18, lines 38-40:

$$\left[\begin{array}{c}CH_2-CH-Y-Z\\ |\quad\quad |\\ COOR\quad COO^-\end{array}\right]_x M_1^{+x}$$ " should be $$--\left[\begin{array}{c}CH_2-CH-Y-Z\\ |\quad\quad |\\ COOR\quad COO^-\end{array}\right]_x M_1^{+x} --.$$

Signed and Sealed this

Twenty-third Day of May 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,058,554

DATED : November 15, 1977

INVENTOR(S) : Eddie N. Gutierrez et al

It is certified that error appears in the above-identified patent and that said Letters Patent are hereby corrected as shown below:

In the Specification:

Column 10, line 58: "B" should read --C--.

Column 10, lines 59-62 change

"The mole ratio of maleate to glycolate is 0.17:1, calcium hydroxide solution is added to the reaction mixture to a pH of 8.6 and the reaction is run for 2-3 hours"

to

--The mole ratio of maleate to glycolate is 0.17:1, the reaction is run for 2-3 hours and calcium hydroxide is added to produce a pH of 8.6 in an aqueous solution prepared from the viscous liquid product which was recovered from the reaction mixture--

Signed and Sealed this

Tenth Day of June 1980

[SEAL]

Attest:

SIDNEY A. DIAMOND

Attesting Officer

Commissioner of Patents and Trademarks